United States Patent
Sineva et al.

(10) Patent No.: US 9,290,700 B2
(45) Date of Patent: Mar. 22, 2016

(54) METHOD FOR PREPARING SYNTHETIC LIQUID HYDROCARBONS FROM CO AND $H_2$

(71) Applicant: Infra XTL Technology Limited, Limassol (CY)

(72) Inventors: Lilia Vadimovna Sineva, Moscow (RU); Vladimir Zalmanovich Mordkovich, Moscow (RU)

(73) Assignee: INFRA XTL TECHNOLOGY LIMITED, Limassol (CY)

( * ) Notice: Subject to any disclaimer, the term of this patent is extended or adjusted under 35 U.S.C. 154(b) by 0 days.

(21) Appl. No.: 14/456,932

(22) Filed: Aug. 11, 2014

(65) Prior Publication Data

US 2016/0040075 A1    Feb. 11, 2016

(51) Int. Cl.
*C10G 2/00*   (2006.01)
*C07C 1/02*   (2006.01)
*C07C 1/04*   (2006.01)

(52) U.S. Cl.
CPC . *C10G 2/332* (2013.01); *C07C 1/02* (2013.01); *C07C 1/04* (2013.01); *C07C 1/0425* (2013.01); *C07C 1/0435* (2013.01); *C07C 1/0485* (2013.01); *C10G 2/32* (2013.01); *C10G 2/331* (2013.01); *C10G 2/334* (2013.01); *C10G 2/33* (2013.01)

(58) Field of Classification Search
CPC ........ C07C 1/02; C07C 1/0485; C07C 1/0425
See application file for complete search history.

(56) References Cited

U.S. PATENT DOCUMENTS

| | | | | |
|---|---|---|---|---|
| 7,973,086 | B1 * | 7/2011 | Saxton et al. | 518/700 |
| 8,119,552 | B2 * | 2/2012 | Burgfels et al. | 502/67 |
| 2012/0108682 | A1 * | 5/2012 | Saxton et al. | 518/707 |

OTHER PUBLICATIONS

Perego, C. et al. "Gas to liquids technologies for natural gas reserves valorization: The Eni experience" 2009, 142, pp. 9-16.*

* cited by examiner

*Primary Examiner* — Jafar Parsa
*Assistant Examiner* — Medhanit Bahta
(74) *Attorney, Agent, or Firm* — Knobbe, Martens, Olson & Bear, LLP

(57) ABSTRACT

The invention relates to synthesis of liquid $C_5$ and higher hydrocarbons from CO and $H_2$ according to the Fischer-Tropsch synthesis. An object is to provide high syngas conversion rate, minimum content of waxes in the products, high content of $C_{10}$-$C_{20}$ fractions per pass within a single reactor and avoidance of use of expensive catalyst components. The claimed method for preparing synthetic liquid hydrocarbons by catalytic conversion of a syngas according to the Fischer-Tropsch synthesis comprises sequential passing the reaction mixture through at least four layers of a multilayer fixed bed of granulated catalysts, wherein a first layer in the direction of passing the reaction mixture comprises a cobalt Fischer-Tropsch synthesis catalyst that provides occurring the Fischer-Tropsch synthesis at Anderson-Schulz-Flory factor of 0.67 to 0.96, a second layer in the direction of passing the reaction mixture comprises a traditional cobalt Fischer-Tropsch synthesis catalyst that provides occurring the Fischer-Tropsch synthesis at Anderson-Schulz-Flory factor of 0.82 to 0.96, a third layer in the direction of passing the reaction mixture comprises not less than 30% of H-form zeolite, and a lowermost layer comprises a traditional cobalt Fischer-Tropsch synthesis catalyst that provides occurring the Fischer-Tropsch synthesis at Anderson-Schulz-Flory factor of 0.82 to 0.96. The cobalt Fischer-Tropsch synthesis catalyst of the first layer has thermal conductivity not less than 4 watt/m·K and comprises not more than 10% of skeleton cobalt to decrease heat generation intensity in the front layer and not less than 20% of H-form zeolite.

6 Claims, No Drawings

METHOD FOR PREPARING SYNTHETIC LIQUID HYDROCARBONS FROM CO AND $H_2$

FIELD OF THE INVENTION

The present invention relates to the fields of petrochemistry, gas chemistry, coal fuel chemistry and is used to synthesize liquid $C_5$ and higher hydrocarbons from CO and $H_2$ according to the Fischer-Tropsch synthesis.

BACKGROUND OF THE INVENTION

The Fischer-Tropsch process discovered the last century and immediately used in industry occurs under high pressure and in the presence of catalysts based on metals of group VIII of the Mendeleev's periodic table. The process is exothermic.

The main requirements for the process, particularly for the arrangement of a catalyst bed for the Fischer-Tropsch process, include high concentration of the catalytically-active component in the reaction volume, small typical size of the catalyst active particles, high effective thermal conductivity of the catalyst bed, developed gas-liquid interface, provision of a convective gas flow regime that should be close to a plug flow regime, and these requirements define a close relationship between the choice of the catalyst and reactor design.

It is known that heterogeneous exothermic processes can be technologically implemented in a fluidized-bed reactor, or in a liquid phase with a suspended catalyst aka slurry-phase bed, or in a fixed bed reactor.

At present, fixed bed reactors are most widely used in the area of catalytic technologies due to simplicity and ripeness of their mechanical design. Such reactors comprise reaction tubes, which in turn contain a heterogeneous system comprising at least two phases, i.e. solid particles of a catalyst and a reaction mixture in the form of gas and/or liquid, which moves among the above-said solid particles. The solid particles of catalyst usually exist as pellets or granules. Both chemical transformations on the catalyst surface and physical processes such as heat- and mass-transfer of reactants and products in the bed take place simultaneously in the reactor.

One of main problems faced by a skilled in the art when developing catalytic tubular reactors for the Fischer-Tropsch synthesis is ensuring high selectivity of the process to the sum of liquid products, and especially selectivity to the most important $C_{10}$-$C_{18}$ fraction that is the basis of diesel and kerosene fuels.

A method for solving this problem is known and described in public literature:
P. M. Maitlis, A. deKlerk (eds.). *Greener Fischer-Tropsch Processes*. Wiley-VCH, Weinheim, 2013. P. 372;
Steynberg A. P., Dry M. E. Fischer-Tropsch Technology.—Elsevier, 2004. V. 64. 722 p.;
J. T. Bartis, F. Camm, D. S. Ortiz. *Producing Liquid Fuels from Coal: Prospects and Policy Issues*. RAND Corporation, 2008. P. 167;
A. deKlerk, E. Furimsky. *Catalysis in the Refining of Fischer-Tropsch Syncrude*. RSC Publishing, Cambridge, UK, 2010. P. 279;
U.S. Pat. No. 7,157,501 (2006).

According to this known method, cobalt Fischer-Tropsch synthesis catalysts are used. These catalysts provide occurring the Fischer-Tropsch synthesis at Anderson-Schulz-Flory factor not less than 0.88 are used. Such catalysts allow to obtain a sum of liquid products with high selectivity, over 80%, however, heavy waxes are the main product, whereas the content of $C_{10}$-$C_{20}$ fraction is less than 40%. In order to compensate for this disadvantage, a hydrocracking reactor is additionally used to ensure wax conversion into lighter hydrocarbons in the presence of hydrogen and by means of a special catalyst.

Another method for solving this problem, which includes combined use of a mixture of granules of a Fischer-Tropsch synthesis catalyst and zeolite granules, is described in the following information sources:
Z.-W. Liu, X. Li, K. Asami, K. Fujimoto. Catal. Today, 104, 41 (2005);
Z.-W. Liu, X. Li, K. Asami, K. Fujimoto. Energy Fuels, 19, 1790 (2005);
T.-Sh. Zhao, J. Chang, Y. Yoneyama, N. Tsubaki. Ind. Eng. Chem. Res., 44, 769 (2005);
A. Freitez, K. Pabst, B. Kraushaar-Czarnetzki, G. Schaub. Ind. Eng. Chem. Rev., 50, 13732 (2011);
US Patent Application No. 2006223893 A1 (2006);
EP Patent No. 1558701 A1 (2003).

Also known are technical solutions using sequential arrangement of a layer of a zeolite-containing catalyst or another catalyst active in hydrocarbon hydrotransformations after a layer of a Fischer-Tropsch synthesis catalyst:
Z.-W. Liu, X. Li, K. Asami, K. Fujimoto. *Appl. Catal. A: Gen.*, 300, 162 (2006);
A. M. Subiranas, G. Schaub. *Int. J. Chem. React. Eng.*, 5, A 78 (2007);
U.S. Pat. No. 7,973,086 B1 (2010);
U.S. Pat. No. 8,519,011 B2 (2013);
KR Patent No. 20100071684 A (2008);
I. Nam. K. M. Cho, J. G. Seo, S. wan Hwang, K.-W. Jun, I. K. Song. *Catal. Lett.*, 130, 192-197 (2009);
US Patent Application No. 2009143220 A1 (2008);
Patent Application WO 2011/090554 (2009);
or granules of a Fischer-Tropsch synthesis catalyst are used in zeolite capsules:
S. Sartipi, J. E. van Dijk, J. Gascon, F. Kaptejn. *Appl. Catal. A: Gen.*, 456, 11 (2013);
G. Yang, Ch. Xing, W. Hirohama, Y. Jin, Ch. Zeng, Y. Suehiro, T. Wang, Y. Yoneyama, N. Tsubaki. *Catal. Today*, 215, 29 (2013);
Yu. Jin, R. Yang, Y. Mori, J. Sun, A. Taguchi, Y. Yoneyama, T. Abe, N. Tsubaki. Appl. Catal. A: Gen., 456, 75 (2013).

The zeolite property to serve as a hydrocracking catalyst and convert resulting waxes into lighter hydrocarbons in situ is used in the above-mentioned known methods using zeolite. Therefore, these methods are often referred to as the use of bifunctional catalysts or the use of hybrid catalysts or the use of bifunctional (hybrid) bed. These methods provide minimum wax content in the product and one-pass formation of light hydrocarbon mixture in a simple, inexpensive reactor. However, these methods are characterized by a low conversion rate of CO and $H_2$ as well as by low yield of the $C_{10}$-$C_{20}$ fraction.

Known in the art is a vertical reactor with a cascade of three sequential fixed catalyst layers for carrying out the Fischer-Tropsch synthesis in the first layer, oligomerization in the second layer and hydrocracking/isomerization in the third layer to obtain middle distillates (Sihe Zhang, Rui Xu, Ed Durham and Christopher B. Roberts. AIChE Journal. V. 60, Issue 7, pp. 2573-2583).

It has been demonstrated that the Fischer-Tropsch synthesis using a multilayer fixed bed leads to decrease of selectivity in the formation of olefins and $C_{26+}$ hydrocarbons as well as notable increase of the yield of branched paraffins and aromatic compounds. The use of supercritical hexane as a reaction medium results in considerable decrease of selectivity in the formation of $CH_4$ and $CO_2$. Besides, significant quantities of aldehydes and cycloparaffins are formed in supercritical conditions. In this reactor, a co-precipitated iron-zinc based catalyst promoted by copper and potassium is used as a Fischer-Tropsch synthesis catalyst, amorphous aluminosilicate is used as a catalyst for the oligomerization reaction, and palladium applied on amorphous aluminosilicate is used as a hydrocracking/isomerization catalyst. The reactor is provided with three heating zones. The temperature of 240° C. is maintained in the upper layer for occurring the Fischer-Tropsch synthesis whereas 200° C. is maintained in the middle layer for the oligomerization reaction and 330° C. is maintained in the lower layer. Hexane is added at the rate of 1 ml/min. The pressure of 76 bars is maintained in the reactor. $H_2$:CO ratio is 1.75. As a result of the syngas passing through the three catalyst layers of the multilayer fixed bed, a mixture of hydrocarbons is formed during CO conversion. The mixture comprises 43 wt % of $C_{12}$-$C_{22}$ and 10 wt % of $C_{22+}$. Disadvantages of this known device are supercritical conditions requiring high energy consumption to create the pressure of 76 bars, high selectivity in $CO_2$ formation (13%), low yield of the target product and high content of waxes.

Known in the art is a porous catalyst comprising palladium on mesoporous aluminium oxide for the Fischer-Tropsch hybrid synthesis. The catalyst is to be used in a continuous device to carry out a dual reaction for the purpose of obtaining $C_{10}$-$C_{20}$ middle distillate (KR Patent 20100071684 A, IPC B0021/04, B0023/44, B01J35/04, B01J37/04, 2008). The device is a dual-chamber reactor. A Co/$TiO_2$ Fischer-Tropsch synthesis catalyst is introduced into the upper chamber. The synthesis occurs at 200-400° C., 5 to 30 bars, syngas flow rate of 100 to 1,000 ml/$g_{cat}$·h$^{-1}$ and $H_2$:CO ratio of 1.5. In the second, downstream chamber, a Pd/$Al_2O_3$ catalyst layer is located. The temperature of 270-350° C. is maintained in this layer. Furthermore, hydrogen is additionally introduced between the chambers. Said reaction results in the formation of hydrocarbon mixtures comprising 30-50 wt % of $C_1$-$C_9$ hydrocarbons, 45-55 wt % of $C_{10}$-$C_{20}$ hydrocarbons and 5-15 wt % of $C_{21+}$ hydrocarbons. A disadvantage of this known solution is complexity of the Fischer-Tropsch hybrid synthesis device that includes two chambers operated at different temperatures, whereas additional quantity of hydrogen needs to be introduced into the second chamber. Other disadvantages are the use of expensive palladium, complicated production of mesoporous aluminium and the yield of target $C_{10}$-$C_{20}$ hydrocarbons of less than 55%.

Known in the art is a method for syngas conversion in a mixture of liquid hydrocarbons used in fuel and petroleum production (U.S. Pat. No. 8,519,011 B2, IPC C07C27/00, 2013). The syngas is brought into contact with at least two layers of a syngas conversion (Fischer-Tropsch synthesis) catalyst and with a subsequent layer of a mixture of hydrocracking and hydroisomerization catalysts or subsequent separate layers of hydrocracking and hydroisomerization catalysts. This process may be carried out within a single reactor at common temperature and common pressure in the reactor. The process ensures high yield of liquid hydrocarbons in the range of $C_5$-$C_{12}$ naphtha (40-80 wt %) and low yield of waxes (less than 5%). A catalyst comprising 20% of Co, 0.5% of Ru and 3% of Zr/$SiO_2$ is used as the syngas conversion catalyst. Pt/H-zeolite is used as the hydrocracking catalyst and Pd/H-zeolite is used as the hydroisomerization catalyst. Disadvantages of this method are use of expensive metals in the composition of the hydrocracking and hydroisomerization catalysts and low syngas conversion rate per pass, which compels to use of recycling that makes the process notably more expensive.

The closest prior art is a process for converting syngas to a hydrocarbon mixture, which includes contacting a feed comprising a mixture of carbon monoxide and hydrogen with at least two layers of a syngas conversion catalyst comprising a metal component, and at least two layers of a hydrocracking catalyst comprising an acidic component, in an alternating arrangement of layers within a single reaction tube, such that the feed sequentially contacts with at least a first layer of the syngas conversion catalyst, a first layer of the hydrocracking catalyst, a second layer of the syngas conversion catalyst and a second layer of the hydrocracking catalyst, thereby resulting in a hydrocarbon mixture which at ambient conditions contains 0-20 wt % of $CH_4$, 0-20 wt % of $C_2$-$C_4$, greater than 70 wt % of $C_{5+}$, 40-80 wt % of $C_5$-$C_{12}$ and 0-5 wt % of $C_{21+}$ n-paraffins (U.S. Pat. No. 7,973,086 B1, IPC C07C27/00, 2011). The size of syngas conversion catalyst particles is 1 to 5 mm and the weight ratio of the active components of the hydrocracking catalyst to the syngas conversion catalyst is 2:1 to 100:1. The weight ratio of the acidic component in the hydrocracking catalyst to the metal component in the syngas conversion catalyst is 0.1:1 to 100:1. The synthesis occurs at 3-30 atm and 160-300° C. The obtained liquid hydrocarbons (naphtha) do not contain waxes and have a cloud point temperature of 15° C. Disadvantages of this known solution are use of expensive metals in the composition of the hydrocracking catalysts and low syngas conversion rate per pass, which compels to use recycling that makes the process notably more expensive.

SUMMARY OF THE INVENTION

A technical object of the present invention is to provide carrying out a process of syngas conversion so that it is possible to ensure not only hydrocarbon growth and cracking long chain molecules of waxes into shorter chain molecules of lighter hydrocarbons but also reprocessing light and superlight ($C_2$-$C_4$) hydrocarbons to longer chain molecules.

A technical result of the present invention is to provide high syngas conversion rate, minimum content of waxes in the products and high content of $C_{10}$-$C_{20}$ fractions per pass within a single reactor. In addition, the present invention allows to avoid the use of expensive catalyst components, namely Pt or Pd precious metals.

Said object is accomplished by that in a method for preparing synthetic liquid hydrocarbons by catalytic conversion of a syngas according to the Fischer-Tropsch synthesis in a multilayer fixed bed of granulated catalysts, according to the present invention, the reaction mixture is sequentially passed through at least four layers of the fixed bed, wherein a first layer in the direction of passing the reaction mixture comprises a cobalt Fischer-Tropsch synthesis catalyst that provides occurring the Fischer-Tropsch synthesis at Anderson-Schulz-Flory factor of 0.67 to 0.96, a second layer in the direction of passing the reaction mixture comprises a traditional cobalt Fischer-Tropsch synthesis catalyst that provides occurring the Fischer-Tropsch synthesis at Anderson-Schulz-Flory factor of 0.82 to 0.96, a third layer in the direction of passing the reaction mixture comprises not less than 30% of H-form zeolite, and a lowermost layer comprises a traditional cobalt Fischer-Tropsch synthesis catalyst that provides occurring the Fischer-Tropsch synthesis at Anderson-Schulz-Flory factor of 0.82 to 0.96.

In a preferred embodiment of the present invention, the cobalt Fischer-Tropsch synthesis catalyst of the first layer has thermal conductivity not less than 4 watt/m·K and comprises not more than 10% of skeleton cobalt to decrease heat generation intensity in the front layer and not less than 20% of H-form zeolite.

The volume relation of the first layer to the second layer is preferably not less than 3:1. The volume relation of the second layer to the third layer is preferably not less than 1.1:1, and the volume relation of the lowermost layer to the third layer is not less than 0.2:1.

In one of preferred embodiments of the present invention, the reaction mixture, after passing through the first layer, is sequentially passed through at least two additional catalyst layers alternating in the following sequence: an upstream additional layer comprising a traditional cobalt Fischer-Tropsch synthesis catalyst that provides occurring the Fischer-Tropsch synthesis at Anderson-Schulz-Flory factor of 0.82 to 0.96 and a downstream additional layer comprising not less than 30% of H-form zeolite.

DETAILED DESCRIPTION OF THE PREFERRED EMBODIMENT

As demonstrated by numerous studies by the authors of the present invention, the results of which are partially referred to in this specification (see Examples below), the optimal result can be achieved due to that the products of the Fischer-Tropsch synthesis mainly consisting of waxes, as well as gaseous products with high content of olefins and some amount of light liquid fractions immediately at the outlet of the catalyst layer can be subject to conversion on polyfunctional H-form zeolite where the following reactions simultaneously occur:

- wax cracking to form $C_3$-$C_{18}$ fraction hydrocarbons, wherein lighter hydrocarbons are mainly olefins;
- formation of isoparaffins and $C_{10}$-$C_{20}$ isoolefins by addition of light olefins to heavier hydrocarbons.

Furthermore, studies by the authors of the present invention have demonstrated that as a result of the arranging, immediately at the H-form zeolite layer outlet, one more layer of the Fischer-Tropsch synthesis catalyst, the following reactions simultaneously occur in this layer:

- the Fischer-Tropsch synthesis of unreacted CO and $H_2$ to form a whole range of products including waxes;
- readsorption of the olefins formed in the preceding layer and additional growth of longer chain molecules of $C_{10}$-$C_{20}$ hydrocarbons as substrates from the olefins;
- hydrogenation of the olefins and isoolefins formed in the H-form zeolite layer.

According to Examples 1 to 8 below, the obtained catalysts were introduced in layers into a steel tubular reactor having the inner diameter of 19 mm. The hydrocarbons synthesis according to Examples 1 to 8 occurred in this reactor under the following conditions: pressure of 2 MPa, temperature of 235° C., $H_2$:CO ratio of 2, syngas space velocity of 2,000 $h^{-1}$. The synthesis results are specified in the table below.

Examples 3 to 8 have been implemented according to the present invention whereas the synthesis results according to Examples 1 to 2 and the prior art (given below Example 8) are presented in the table as comparison to confirm the positive technical results when implementing the method according to the present invention.

Example 1

Comparative

Preparing a Fischer-Tropsch Synthesis Catalyst (FT Catalyst)

The catalyst comprising 20% of Co and 80% of $Al_2O_3$ in the amount of 4.4 g was prepared as follows:

3.52 g of aluminium oxide (SASOL) granules of the size of 2.5×2 5 mm were impregnated with a water solution of $Co(NO_3)_2 \cdot 6H_2O$ (2.17 g of $Co(NO_3)_2 \cdot 6H_2O$+1.5 ml of $H_2O$) during 0.5 hours with further drying in a water bath for 1 hour and calcinating in an air stream at 400° C. for 5 hours. The semi-finished product was cooled to the room temperature then the impregnating, drying and calcinating procedures were repeated.

The obtained catalyst was loaded as a fixed bed into the steel tubular reactor.

Example 2

Comparative

Preparing a Fischer-Tropsch Synthesis Catalyst

The catalyst comprising 20% of Co and 80% of $Al_2O_3$ in the amount of 4.4 g was prepared according to Example 1.

H-zeolite HY CBV 720 (Zeolyst International) was used in the form of granules of the size of 2.5×2.5 mm in the amount of 4 g.

The catalysts were loaded into the reactor to form a multilayer fixed bed having following layered sequence: a lower layer of 5 $cm^3$ (4 g) of H-zeolite HY, and a layer of 5.5 $cm^3$ (4.4 g) of the Fischer-Tropsch synthesis catalyst above zeolite.

Example 3

Preparing a Fischer-Tropsch Synthesis Catalyst

The catalyst comprising 20% of Co and 80% of $Al_2O_3$ in the amount of 17.6 g was prepared according to Example 1 but by selecting appropriate amounts of the ingredients.

H-zeolite HY CBV 720 (Zeolyst International) was used in the form of granules of the size of 2.5×2.5 mm in the amount of 4 g.

The Fischer-Tropsch synthesis catalyst comprising 20% of Co and 80% of $Al_2O_3$ in the amount of 2 g was prepared as described above but by selecting appropriate amounts of the ingredients.

All the obtained catalysts were loaded into the reactor to form a multilayer fixed bed having the following layered sequence: a lowermost layer of 2.5 $cm^3$ (2 g) of the Fischer-Tropsch synthesis catalyst, a 5 $cm^3$ (4 g) layer of H-zeolite HY above the lowermost layer, a 5.5 $cm^3$ (4.4 g) layer of the Fischer-Tropsch synthesis catalyst above the zeolite layer, and an uppermost layer of 16.5 $cm^3$ (13.2 g) of the Fischer-Tropsch synthesis catalyst.

Example 4

Preparing a Catalyst Comprising 10% of Co and 20% of H-Zeolite

The catalyst comprising 10% of Co, 20% of HB zeolite, 50% of Al and 20% of AlOOH in the amount of 13.2 g was prepared as follows:

2.64 g of AlOOH (Dispersal P2, SASOL), 2.64 g of HB zeolite (CP 814C, Zeolyst International), 6.6 g of Al powder (PAP-2, RUSAL) and 1.32 g of cobalt powder (from $Co_2Al_9$ alloy, Alfa Aesar, A Johnson Matthey Company) were mixed with a liquid phase comprising 0.59 ml of $HNO_3$ (64%), 8 ml of distilled water and 1.98 g of triethylene glycol (TEG) to form a homogeneous mix and were introduced into an extruder, the die diameter of which was 2.5 mm. The obtained granules were held in air at the room temperature for 10 hours and calcined in a muffle kiln when increasing temperature from 25 to 450° C. at the rate of 18° C./h and holding for 4 hours at 450° C. The granules were then cooled to the room temperature and crushed to the particle size of 2.5×2.5 mm Preparing the Fischer-Tropsch Synthesis Catalyst The catalyst comprising 20% of Co and 80% of $Al_2O_3$ in the amount of 4.4 g was prepared according to Example 1.

H-zeolite HY CBV 720 (Zeolyst International) was used in the form of granules of the size of 2.5×2.5 mm in the amount of 4 g.

The Fischer-Tropsch synthesis catalyst comprising 20% of Co and 80% of $Al_2O_3$ in the amount of 2 g was prepared as described above but by selecting appropriate amounts of the ingredients.

All the obtained catalysts were loaded into the reactor to form a multilayer fixed bed having the following layered sequence: a lowermost layer of 2.5 $cm^3$ (2 g) of the Fischer-Tropsch synthesis catalyst, a 5 $cm^3$ (4 g) layer of H-zeolite HY above the lowermost layer, a 5.5 $cm^3$ (4.4 g) layer of the Fischer-Tropsch synthesis catalyst above the zeolite layer and an uppermost layer of 16.5 $cm^3$ (13.2 g) of the catalyst comprising 10% of Co and 20% of H-zeolite.

Example 5

Preparing the Catalyst Comprising 10% of Co and 20% of H-Zeolite

The catalyst comprising 10% of Co, 20% of HB zeolite, 50% of Al and 20% of AlOOH in the amount of 13.2 g was prepared according to Example 4.

Preparing the Fischer-Tropsch Synthesis Catalyst

The catalyst comprising 20% of Co and 80% of $Al_2O_3$ in the amount of 4.4 g was prepared according to Example 1.

H-zeolite HZSM-5 CBV 3024E (Zeolyst International) was used in the form of granules of the size of 2.5×2.5 mm in the amount of 4 g.

The Fischer-Tropsch synthesis catalyst comprising 20% of Co and 80% of $Al_2O_3$ in the amount of 4 g was prepared as described above but by selecting appropriate amounts of the ingredients.

All the obtained catalysts were loaded into the reactor to form a multilayer fixed bed having the following layered sequence: a lowermost layer of 5 $cm^3$ (4 g) of the Fischer-Tropsch synthesis catalyst, a 5 $cm^3$ (4 g) layer of H-zeolite HZSM-5 above the lowermost layer, a 5.5 $cm^3$ (4.4 g) layer of the Fischer-Tropsch synthesis catalyst above the zeolite layer, and an uppermost layer of 16.5 $cm^3$ (13.2 g) of the catalyst comprising 10% of Co and 20% of H-zeolite.

Example 6

Preparing a Catalyst Comprising 7.5% of Co and 20% of H-Zeolite

The catalyst comprising 7.5% of Co, 20% of HB zeolite, 50% of Al and 22.5% of AlOOH in the amount of 20 g was prepared as follows:

4.5 g of AlOOH (Dispersal P2, SASOL), 4 g of HB zeolite (CP 814C, Zeolyst International), 10 g of Al powder (PAP-2, RUSAL) and 1.5 g of cobalt powder (from $Co_2Al_9$ alloy, Alfa Aesar, A Johnson Matthey Company) were mixed with a liquid phase comprising 0.9 ml of $HNO_3$ (64%), 11 ml of distilled water and 3 g of triethylene glycol (TEG) to form a homogeneous mix and were introduced into an extruder, the die diameter of which was 2.5 mm. Further steps were identical to those described in Example 4.

Preparing the Fischer-Tropsch Synthesis Catalyst

The catalyst comprising 20% of Co and 80% of $Al_2O_3$ in the amount of 6 g was prepared as described above but by selecting appropriate amounts of the ingredients.

H-zeolite HY CBV 720 (Zeolyst International) was used in the form of granules of the size of 2.5×2.5 mm in the amount of 4 g.

The Fischer-Tropsch synthesis catalyst comprising 20% of Co and 80% of $Al_2O_3$ in the amount of 0.8 g was prepared as described above but by selecting appropriate amounts of the ingredients.

All the obtained catalysts were loaded into the reactor to form a multilayer fixed bed having the following layered sequence: a lowermost layer of 1 $cm^3$ (0.8 g) of the Fischer-Tropsch synthesis catalyst, a 5 $cm^3$ (4 g) layer of H-zeolite HY above the lowermost layer, a 7.5 $cm^3$ (6 g) layer of the Fischer-Tropsch synthesis catalyst above the zeolite layer, and the uppermost layer of 25 $cm^3$ (20 g) of the catalyst comprising 7.5% of Co and 20% of H-zeolite.

Example 7

Preparing the Catalyst Comprising 10% of Co and 20% of H-Zeolite

The catalyst comprising 10% of Co, 20% of HB zeolite, 50% of Al and 20% of AlOOH in the amount of 17.6 g was prepared as described in Example 4 but by selecting appropriate amounts of the ingredients.

Preparing the Fischer-Tropsch Synthesis Catalyst

The catalyst comprising 20% of Co and 80% of $Al_2O_3$ in the amount of 4.4 g was prepared according to Example 1.

H-zeolite H-Mordenite CBV 21A (Zeolyst International) was used in the form of granules of the size of 2.5×2.5 mm in the amount of 4 g.

The Fischer-Tropsch synthesis catalyst comprising 20% of Co and 80% of $Al_2O_3$ in the amount of 8 g was prepared as described above but by selecting appropriate amounts of the ingredients.

All the obtained catalysts were loaded into the reactor to form a multilayer fixed bed having the following layered sequence: a lowermost layer of 10 $cm^3$ (8 g) of the Fischer-Tropsch synthesis catalyst, a 5 $cm^3$ (4 g) layer of H-zeolite H-Mordenite above the lowermost layer, a 5.5 $cm^3$ (4.4 g) layer of the Fischer-Tropsch synthesis catalyst above the zeolite layer, and the uppermost layer of 22 $cm^3$ (17.6 g) of the catalyst comprising 10% of Co and 20% of H-zeolite.

Example 8

Preparing the Catalyst Comprising 10% of Co and 20% of H-Zeolite

The catalyst comprising 10% of Co, 20% of HB zeolite, 50% of Al and 20% of AlOOH in the amount of 13.2 g was prepared according to Example 4.

Preparing the Fischer-Tropsch Synthesis Catalyst

The catalyst comprising 20% of Co and 80% of $Al_2O_3$ in the amount of two portions of 4.4 g each was prepared as follows:

7.04 g of aluminium oxide (SASOL) granules of the size of 2.5×2.5 mm were impregnated with a water solution of $Co(NO_3)_2 \cdot 6H_2O$ (4.34 g of $Co(NO_3)_2 \cdot 6H_2O$ + 3 ml of $H_2O$) for 0.5 hours with further drying in a water bath for 1 hour and calcinating in an air stream at 400° C. for 5 hours. The semi-finished product was cooled to the room temperature then the impregnating, drying and calcinating procedures were repeated. The mix of the obtained catalyst was divided into two equal portions.

H-zeolite HB CP 814C (Zeolyst International) was used in the form of granules of the size of 2.5×2.5 mm in the amount of two portions of 4 g each.

The Fischer-Tropsch synthesis catalyst comprising 20% of Co and 80% of $Al_2O_3$ in the amount of 2 g was prepared as described above but by selecting appropriate amounts of the ingredients.

All the obtained catalysts were loaded into the reactor to form a multilayer fixed bed having the following layered sequence: a lowermost layer of 2.5 cm³ (2 g) of the Fischer-Tropsch synthesis catalyst, a 5 cm³ (4 g) layer of H-zeolite HB above the lowermost layer, a 5.5 cm³ (4.4 g) layer of the Fischer-Tropsch synthesis catalyst above the zeolite layer, then one more 5 cm³ (4 g) layer of H-zeolite HB, then one more 5.5 cm³ (4.4 g) layer of the Fischer-Tropsch synthesis catalyst above zeolite, and the uppermost layer of 16.5 cm³ (13.2 g) of the catalyst comprising 10% of Co and 20% of H-zeolite.

TABLE

Synthesis results

| Example | Number of layers | Sequence of layers in the reactor (from top to bottom) | Volume relations of layers | CO conversion, mol % | $C_{21+}$ wt % | $C_{10}$-$C_{20}$ wt % |
|---|---|---|---|---|---|---|
| 1 | 1 | FT catalyst | 1 | 40 | 40 | 37 |
| 2 | 2 | FT catalyst<br>H-zeolite | 1.1:1 | 31 | 13 | 48 |
| 3 | 4 | FT catalyst<br>FT catalyst<br>H-zeolite<br>FT catalyst | 3.3:1.1:1:0.5 | 77 | 8 | 50 |
| 4 | 4 | 10% of Co + 20% of H-zeolite<br>FT catalyst<br>H-zeolite<br>FT catalyst | 3.3:1.1:1:0.5 | 85 | 0 | 55 |
| 5 | 4 | 10% of Co + 20% of H-zeolite<br>FT catalyst<br>H-zeolite<br>FT catalyst | 3.3:1.1:1:1 | 92 | 1 | 59 |
| 6 | 4 | 10% of Co Co + 20% of H-zeolite<br>FT catalyst<br>H-zeolite<br>FT catalyst | 5:1.5:1:0.2 | 90 | 0.5 | 58 |
| 7 | 4 | 7.5% of Co + 20% of H-zeolite<br>FT catalyst<br>H-zeolite<br>FT catalyst | 4.4:1.1:1:2 | 94 | 2 | 61 |
| 8 | 6 | 10% of Co + 20% of H-zeolite<br>FT catalyst<br>H-zeolite<br>FT catalyst<br>H-zeolite<br>FT catalyst | 3.3:1.1:1:1.1:1:0.5 | 96 | 0.5 | 66 |
| Prior art: AIChE Journal. V. 60, pp. 2573-2583 (240° C. + 200° C., + 330° C., 76 bar) | 3 | FT catalyst<br>Oligomerization catalyst<br>Hydrocracking/ isomerization catalyst | 1:1:1 (weight relations) | 84 | 10 ($C_{22+}$) | 43 ($C_{12}$-$C_{22}$) |
| Prior art: KR (220° C. + 330° C., 10-12 bar, $H_2$:CO = 1.5) | 2 | FT catalyst<br>Pd-$Al_2O_3$ | 1:1 (weight relations) | — | 25 | 49 |
| Prior art: U.S. Pat. No. 8,519,011 (220° C., 20 bar, $H_2$:CO = 1.5) | 6 | FT catalyst<br>Hydrocracking catalyst<br>Hydroisomerization catalyst<br>FT catalyst<br>Hydrocracking catalyst<br>Hydroisomerization catalyst | 1:1.3:1.3:1:1.3:1.3 (weight relations) | 29 | 8 | 37 |

TABLE-continued

Synthesis results

| Example | Number of layers | Sequence of layers in the reactor (from top to bottom) | Volume relations of layers | CO conversion, mol % | $C_{21+}$ wt % | $C_{10}$-$C_{20}$ wt % |
|---|---|---|---|---|---|---|
| The closest prior art: U.S. Pat. No. 7,973,086 (220° C., 10 bar, $H_2$:CO = 2) | 6 | FT catalyst<br>0.5% Pd/H-zeolite<br>FT catalyst<br>0.5% Pd/H-zeolite<br>FT catalyst<br>0.5% Pd/H-zeolite | 1:3.2:1:3.2:1:3.2 (weight relations) | 28 | 4 | 36 |

What is claimed is:

1. A method for preparing synthetic liquid hydrocarbons by catalytic conversion of a syngas according to the Fischer-Tropsch synthesis in a multilayer fixed bed of granulated catalysts comprising:
   passing a reaction mixture sequentially through at least four layers of said fixed bed, wherein:
   a first layer in the direction of passing the reaction mixture comprises a cobalt Fischer-Tropsch synthesis catalyst that comprises skeleton cobalt and that catalyzes Fischer-Tropsch synthesis at an Anderson-Schulz-Flory factor of 0.67 to 0.96, wherein the first layer has thermal conductivity of not less than 4 W/m/K,
   a second layer in the direction of passing the reaction mixture comprises a cobalt Fischer-Tropsch synthesis catalyst that catalyzes Fischer-Tropsch synthesis at an Anderson-Schulz-Flory factor of 0.82 to 0.96,
   a third layer in the direction of passing the reaction mixture comprises not less than 30% of H-form zeolite, and
   a lowermost layer comprises a cobalt Fischer-Tropsch synthesis catalyst that catalyzes Fischer-Tropsch synthesis at an Anderson-Schulz-Flory factor of 0.82 to 0.96.

2. The method of claim 1, wherein the cobalt Fischer-Tropsch synthesis catalyst of said first layer comprises not more than 10% of skeleton cobalt to decrease heat generation intensity in the first layer and not less than 20% of H-form zeolite.

3. The method of claim 2, wherein the volume relation of the first layer to the second layer is not less than 3:1.

4. The method of claim 2, wherein the volume relation of the second layer to the third layer is not less than 1.1:1.

5. The method of claim 2, wherein the volume relation of the lowermost layer to the third layer is not less than 0.2:1.

6. The method of claim 1, wherein the reaction mixture, after passing through the first layer, is sequentially passed through at least two additional catalyst layers alternating in the following sequence: an upstream additional layer comprising a cobalt Fischer-Tropsch synthesis catalyst that catalyzes Fischer-Tropsch synthesis at an Anderson-Schulz-Flory factor of 0.82 to 0.96 and a downstream additional layer comprising not less than 30% of H-form zeolite.

* * * * *